(12) United States Patent
Siddik et al.

(10) Patent No.: US 7,271,161 B2
(45) Date of Patent: Sep. 18, 2007

(54) PLATINUM COMPLEXES AS ANTITUMOR AGENTS IN COMBINATION WITH BIOCHEMICAL MODULATION

(75) Inventors: Zahid H. Siddik, Houston, TX (US); Abdul R. Khokhar, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 420 days.

(21) Appl. No.: 10/655,657

(22) Filed: Sep. 5, 2003

(65) Prior Publication Data

US 2004/0097423 A1 May 20, 2004

Related U.S. Application Data

(60) Provisional application No. 60/409,813, filed on Sep. 11, 2002.

(51) Int. Cl.
| | |
|---|---|
| A61P 35/00 | (2006.01) |
| A61K 31/555 | (2006.01) |
| A61K 31/28 | (2006.01) |
| C07D 223/00 | (2006.01) |
| C07D 211/00 | (2006.01) |

(52) U.S. Cl. .............. 514/184; 514/188; 514/217.12; 514/315; 514/492; 540/541; 540/609; 546/11; 546/246

(58) Field of Classification Search ............ 514/184, 514/188, 217.12, 315, 492; 540/541, 609; 546/11, 246

See application file for complete search history.

(56) References Cited

U.S. PATENT DOCUMENTS

| | | | |
|---|---|---|---|
| 4,177,263 A | 12/1979 | Rosenberg et al. | ......... 424/131 |
| 4,902,797 A | 2/1990 | Totani et al. | ................. 546/11 |

OTHER PUBLICATIONS

Anderson and Meister, "Transport and direct utilization of γ-glutamylcyst(e)ine for glutathione synthesis," Proc. Natl. Acad. Sci., USA, 80:707-711, 1983.
Anderson, "Glutathione and glutathione delivery compounds," Adv. Pharmacol., 38:65-78, 1997.
Baranczyk-Kuzma et al., "Tricyclic antidepressants as inhibitors of brain glutathione-S-transferase," Pol Merkuriusz Lek., 11(66):472-475, 2001.
Burg et al., "Peptidomimetic glutathione analogues as novel γGT stable GST inhibitors," Bioog. Med. Chem., 10(1):195-205, 2002.
Campbell et al., "Analytical and preparative separation of the diastereomers of L-buthionine (SR)-sulfoximine, a potent inhibitor of glutathione biosynthesis," Anal. Biochem., 194:268-277, 1991.
Comess et al., "Replication inhibition and translesion synthesis on templates containing site-specifically placed cis-diamminedichloroplatinum (II) DNA adducts," Biochemistry, 31:3975-3990, 1992.

Eastman, "The mechanism of action of cisplatin: from adducts to apoptosis," In: Cisplatin. Chemistry and Biochemistry of a Leading Anticancer Drug, Lippert (ed.), Wiley-VCH, Zürich, Switzerland, 111-134, 1999.
Griffith and Meister, "Potent and specific inhibition of glutathione synthesis by buthionine sufoximine (S-n-Butyl homocysteine sulfoximine)," J. Biol. Chem., 254(16):7558-7560, 1979.
Griffith, "Mechanism of action, metabolism, and toxicity of buthionine sulfoximine and its high homologs, potent inhibitors of glutathione synthesis," J. Biol. Chem., 257(22):13704-13712, 1982.
Jamieson and Lippard, "Structure, recognition, and processing of cisplatin-DNA adducts," Chem. Rev., 99:2467-2498, 1999.
Johnson et al., "Metal antitumor compounds: the mechanism of action of platinum complexes," Prog. Clin. Biochem. Med., 10:1-24, 1989.
Kunze, "Phosphono analogues of glutathione as new inhibitors of glutathione S-transferases," Arch. Pharm., 329(11):503-509, 1996.
Lepre and Lippard, "Interaction of platinum antitumor compounds with DNA," Nucleic Acids Mol. Biol., 4:9-38, 1990.
Meister and Anderson, "Glutathione," Annl. Rev. Biochem., 52:711-760, 1983.
O'Dwyer et al., In: Cisplatin. Chemistry and Biochemistry of a Leading Anticancer Drug, Lipert (ed.), Wiley-VCH, Zürich, Switzerland, 31-72, 1999.
Reedijk, "Improved understanding in platinum antitumor chemistry," Chem. Commun., 801-806, 1996.
Richman and Meister, "Regulation of γ-glutamyl-cystiene synthetase by nonallosteric feedback inhibition by glutathione," J. Biol. Chem., 250(4):1422-1426, 1973.
Rosenberg, "Platinum complexes for the treatment of cancer: why the search goes on," In: Cisplatin. Chemistry and Biochemistry of a Leading Anticancer Drug, Lipert (ed.), Wiley-VCH, Zürich, Switzerland, 3-30, 1999.
Schultz et al., "Inhibitors of glutathione S-transferases as therapeutic agents," Adv. Drug Deliv. Rev., 26(2-3):91-104, 1997.
Tew, "Glutathione-associated enzymes in anticancer drug resistance," Cancer Res., 54(16):4313-4320, 1994.
Zamble and Lippard, "The response of cellular proteins to cisplatin-damaged DNA," In: Cisplatin. Chemistry and Biochemistry of a Leading Anticancer Drug, Lipert (ed.), Wiley-VCH, Zürich, Switzerland, 73-110, 1999.
Siddik et al., "Ammine/amine platinum (II) complexes effective in vivo against murine tumors sensitive or resistant to cisplatin and tetraplatin," J Cancer Res Clin Oncol, 120:571-577, 1994.

Primary Examiner—Brenda Coleman
(74) Attorney, Agent, or Firm—Fulbright & Jaworski L.L.P.

(57) ABSTRACT

The present invention concerns the use of methods and compositions for the treatment of cancer and other hyperproliferative diseases. In certain embodiments, methods are described for the treatment of cancer and/or hyperproliferative diseases by administration of compositions containing at least one platinum complex alone or in combination with a modulator of glutathione. In particular, the methods may be used to treat cisplatin or carboplatin resistant tumor cells.

34 Claims, 2 Drawing Sheets

Chemical Identity of Platinum Complexes

| Complex # | Cemical Name |
|---|---|
| 1 | *cis*-diamino-dichloro-platinum(II) (cisplatin) |
| 2 | *trans*-1R,2R-diaminocyclohexane-dichloro-platinum(II) |
| 3 | Ammine/cyclopropylamine-dichloro-platinum(II) |
| 4 | Ammine/cyclobutylamine-dichloro-platinum(II) |
| 5 | Ammine/cyclopentylamine-dichloro-platinum(II) |
| 6 | Ammine/cyclohexylamine-dichloro-platinum(II) |
| 7 | Ammine/cycloheptylamine-dichloro-platinum(II) |
| 8 | Ammine/cyclooctylamine-dichloro-platinum(II) |
| 9 | Ammine/azetidine-dichloro-platinum(II) |
| 10 | Ammine/pyrrolidine-dichloro-platinum(II) |
| 11 | Ammine/piperidine-dichloro-platinum(II) |
| 12 | Ammine/hexamethyleneimine-dichloro-platinum(II) |
| 13 | *trans*-1R,2R-1S,2S-diaminocyclohexane-tetrachloro-platinum(IV) (tetraplatin) |
| 14 | *trans*-dihydroxo-*trans*-1R,2R-diaminocyclohexane-dichloro-platinum(IV) |
| 15 | Ammine/cyclohexylamine-tetrachloro-platinum(IV) |
| 16 | *trans*-dihydroxo-ammine/cyclohexylamine-dichloro-platinum(IV) |
| 17 | Ammine/hexamethyleneimine-tetrachloro-platinum(IV) |
| 18 | *trans*-dihydroxo-ammine/hexamethyleneimine-dichloro-platinum(IV) |
| 19 | *trans*-diacetato-ammine/hexamethyleneimine-dichloro-platinum(IV) |

PLATINUM COMPLEXES AS ANTITUMOR AGENTS IN COMBINATION WITH BIOCHEMICAL MODULATION

The present application claims priority to U.S. Provisional Patent Application Ser. No. 60/409,813 filed Sep. 11, 2002. The entire text of the above-referenced disclosure is specifically incorporated herein by reference without disclaimer.

The government may own rights in the present invention pursuant to grant number RO1CA50380 from the National Cancer Institute.

BACKGROUND OF THE INVENTION

1. Field of the Invention

The present invention relates generally to the field of cancer therapy. More particularly, it concerns formulations and methods for the treatment of cancer patients using compositions including specific platinum complexes and/or inhibitors of glutathione (GSH) synthesis or activity, such as L-buthionine-sulfoximine (BSO).

2. Description of Related Art

Cisplatin is one of the most effective and broadly used anticancer drugs. Apoptosis induced by cisplatin is generally considered to be mediated by the formation of covalent DNA adducts, which block replication and transcription. Cisplatin (cis-diamminedichloroplatinum) has been used as a chemotherapeutic agent for many years. Rosenberg et al., U.S. Pat. No. 4,177,263, describes methods of treating cancer using cisplatin and cisplatin analogs. The compounds were effective for treating leukemia and tumors induced in mice. Cisplatin and an analog, carboplatin, are now among the most widely used anticancer drugs.

Platinum-based antitumor agents (e.g., cisplatin and carboplatin) play critical roles in the treatment of several cancers. One of the major limitations to these treatments is relapse in a majority of patients, which fail subsequent treatment with platinum agents due to drug resistant tumor cells. This limitation has resulted in an effort to identify platinum analogs that are effective against resistant tumors. Indeed several such analogs (e.g., oxaliplatin and JM216) have entered clinical trials. However, little or no knowledge of the effective mode of action of these analogs is known. Although reduced drug accumulation, increased intracellular glutathione, and increased DNA adduct repair are usually identified as key mechanisms of resistance for cisplatin, satisfactory explanations for reversal of resistance by analogs have not been provided.

Attempts have been made to increase the effectiveness or sensitize resistant tumor cells to cisplatin or analogs thereof by administering the drug in combination with sulfoximines, for example D,L-buthionine-S,R-sulfoximine (BSO) or other agents. The effects of BSO on cytotoxicity and DNA cross-linking induced by bifunctional DNA-reactive cytostatic agents in a human melanoma cell line (RPMI 8322) have been investigated. BSO pretreatment enhanced cytotoxicity of melphalan and nitrogen mustard. A small but significant potentiation by BSO of cisplatin toxicity was also seen (dose modification factor (DMF) of 1.5). The findings supported the hypothesis that the potentiation of the cytotoxicity of bifunctional alkylating agents by BSO is due to increased DNA cross-linking caused by a reduced intracellular conjugation of drug with glutathione.

None of the methods for the treatment of cancer, are entirely satisfactory, thus new and improved methods and compositions for the treatment of cancer are needed.

SUMMARY OF THE INVENTION

Platinum complexes, as described herein, alone or in combination with inhibitors of GSH synthesis or activity (e.g., BSO) show an enhancement of antitumor activity and selectivity for cisplatin-resistant cells. In certain embodiments, the activity of platinum complexes of the invention may be greater against resistant cells than against sensitive cells.

In certain embodiments of the invention the compounds ammine/cycloheptylamine-dichloro-platinum(II), ammine/piperidine-dichloro-platinum(II), ammine/hexamethylene-imine-dichloro-platinum(II), and/or ammine/hexamethyleneimine-tetrachloro-platinum(IV) may be used alone or in combination with inhibitors of GSH synthesis and/or activity for the treatment of a patient with cancer or a hyperproliferative condition.

In various embodiments, an antitumor formulation or composition may include a compound represented by the structural formula:

Structural Formula I or salts thereof. The formulation or composition may also include a negative modulator of glutathione. The negative modulator of glutathione may be an inhibitor of glutathione synthesis. The inhibitor of glutathione synthesis may be L-buthionine-sulfoximine (BSO). BSO may include one or more isomer of BSO.

In other embodiments, an antitumor formulation or composition may include a compound represented by the structural formula:

Structural Formula II or salts thereof. The formulation or composition may also include a negative modulator of glutathione. The negative modulator of glutathione may be an inhibitor of glutathione synthesis. The inhibitor of glutathione synthesis may be L-buthionine-sulfoximine (BSO). BSO may include one or more isomer of BSO.

In still other embodiments, an antitumor formulation or composition may include a compound represented by the structural formula:

Structural Formula III or salts thereof. The formulation or composition may also include a negative modulator of glutathione. The negative modulator of glutathione may be an inhibitor of glutathione synthesis. The inhibitor of glutathione synthesis may be L-buthionine-sulfoximine (BSO). BSO may include one or more isomer of BSO.

In still other embodiments, an antitumor formulation or composition may include a compound represented by the structural formula IV:

Structural Formula IV or salts thereof. The formulation or composition may also include a negative modulator of glutathione. The negative modulator of glutathione may be an inhibitor of glutathione synthesis. The inhibitor of glutathione synthesis may be L-buthionine-sulfoximine (BSO). BSO may include one or more isomer of BSO.

In certain embodiments, a pharmaceutical composition may include one or more platinum complex of ammine/cycloheptylamine-dichloro-platinum(II), ammine/piperidine-dichloro-platinum(II), ammine/hexamethyleneimine-dichloro-platinum(II), or ammine/hexamethyleneimine-tetrachloro-platinum(IV).

The pharmaceutical formulations or compositions of the invention may include a platinum complex in the approximate range of 0.1, 0.5, 1, 2, 3, 4, 5, 6, 7, 8, 9, 10, 11, 12, 13, 14, 15 mM to 5, 6, 7, 8, 9, 10, 11, 12, 13, 14, 15, 16, 17, 18, 19, 20, 25, 30, 40, 50 mM. Pharmaceutical formulations or compositions of the present invention may comprise a biologic modifier of glutathione. The biologic modifier of glutathione may be an inhibitor of glutathione synthesis, such as L-buthionine-sulfoximine. A pharmaceutical composition may include L-buthionine-sulfoximine in the approximate range of 1, 2, 3, 4, 5, 6, 7, 8, 9, 10, 11, 12, 13, 14, 15, 16, 17, 18, 19, 20, 25, 30, 35, 40, 45, 50, 55, 60, 65, 75, 80, 85, 90, 95 µM, to 100, 150, 200, 250, 300, 400, 500 µM or more. A pharmaceutical composition of the invention may be administered intravascularly, orally, intrperitoneally, or by other routes of administration known for platinum complexes and the like.

In yet other embodiments of the invention, a method of inhibiting the proliferation of a cisplatin-resistant cell comprising providing, contacting or administering to a cell ammine/cycloheptylamine-dichloro-platinum(II), ammine/piperidine-dichloro-platinum(II), ammine/hexamethyleneimine-dichloro-platinum(II), or ammine/hexamethyleneimine-tetrachloro-platinum(IV) is contemplated. The method may also include providing a biologic modifier of glutathione. The biologic modifier of glutathione may be an inhibitor of glutathione synthesis, such as one or more isomer of L-buthionine-sulfoximine. In particular embodiments of the invention, the cell is located in a subject such as a mammal. The mammal may be a human or a mouse.

Various embodiments include, a method of treating a cancer cell comprising providing, contacting or administering to the cancer cell ammine/cycloheptylamine-dichloro-platinum(II), ammine/piperidine-dichloro-platinum(II), ammine/hexamethyleneimine-dichloro-platinum(II), or ammine/hexamethyleneimine-tetrachloro-platinum(IV). The method may also include providing a biologic modifier of glutathione. The biologic modifier of glutathione may be an inhibitor of glutathione synthesis, such as one or more isomer of L-buthionine-sulfoximine.

Still other embodiments of the invention include, a method of enhancing anti-tumor activity comprising providing, contacting, or administering a composition comprising a platinum complex selected from the group consisting of ammine/cycloheptylamine-dichloro-platinum(II), ammine/piperidine-dichloro-platinum(II), ammine/hexamethylene-imine-dichloro-platinum(II), and ammine/hexamethylene-imine-tetrachloro-platinum(IV) in combination with an inhibitor of glutathione synthesis. The inhibitor of glutathione synthesis may be further defined as one or more isomer of L-buthionine-sulfoximine. The concentration of L-buthionine-sulfoximine may be in the approximate range of 1, 2, 3, 4, 5, 6, 7, 8, 9, 10, 11, 12, 13, 14, 15, 16, 17, 18, 19, 20, 25, 30, 35, 40, 45, 50, 55, 60, 65, 75, 80, 85, 90, 95 µM, to 100, 150, 200, 250, 300, 400, 500 µM or more.

Additional embodiments of the invention include, a method of making ammine/cycloheptylamine-dichloro-platinum(II) comprising: a) treating an aqueous 20 mmol solution of $K_2PtCl_4$ with 200 mmol KI with stirring for 10 min at room temperature; b) adding two equivalents of cycloheptylamine dropwise and stirring for 30 minutes forming a cis-$Pt^{II}$(c-$C_7H_{11}NH_2$)$_2I_2$ precipitate; c) filtering and washing the cis-$Pt^{II}$(c-$C_7H_{11}NH_2$)$_2I_2$ precipitate with water; d) recrystallizing the cis-$Pt^{II}$(c-$C_7H_{11}NH_2$)$_2I_2$ precipitate from a DMF/$H_2O$ mixture and washing with water, methanol, and ethyl ether; e) drying the cis-$Pt^{II}$(c-$C_7H_{11}NH_2$)$_2I_2$ precipitate in vacuo; f) suspending the dried cis-$Pt^{II}$(c-$C_7H_{11}NH_2$)$_2I_2$ precipitate in 50 mL of 60 to 70% $HClO_4$ and adding 150 mL of ethanol to the suspension with stirring at room temperature forming a brown [$Pt^{IV}$(c-$C_7H_{11}NH_2$)$I_2$]$_2$ precipitate; g) filtering the brown [$Pt^{IV}$(c-$C_7H_{11}NH_2$)$I_2$]$_2$ precipitate and washing the brown [$Pt^{IV}$(c-$C_7H_{11}NH_2$)$I_2$]$_2$ precipitate with water; h) drying the washed brown [$Pt^{II}$(c-$C_7H_{11}NH_2$)$I_2$]$_2$ precipitate in vacuo; i) mixing 5 mmol of brown [$Pt^{II}$(c-$C_7H_{11}NH_2$)$I_2$]$_2$ precipitate with 5 mL of 1.5M $NH_4OH$ in 25 mL of water and stirring the mixture at room temperature overnight forming a yellow cis-$Pt^{II}$($NH_3$)(c-$C_7H_{11}NH_2$)$I_2$ precipitate; j) filtering the yellow cis-$Pt^{II}$($NH_3$)(c-$C_7H_{11}NH_2$)$I_2$ precipitate and washing with water; k) drying the washed yellow cis-$Pt^{II}$($NH_3$)(c-$C_7H_{11}NH_2$)$I_2$ precipitate in vacuo; l) mixing 4 mmol of cis-$Pt^{II}$($NH_3$)(c-$C_7H_{11}NH_2$)$I_2$ with 7.4 mmol of $AgNO_3$ in 200 mL of water and stirring overnight in the dark forming an AgI precipitate; m) removing AgI precipitate by filtration through celite forming a cis-$Pt^{II}$($NH_3$)(c-$C_7H_{11}NH_2$)$NO_3$ filtrate; n) adding 10 mL of concentrated HCl the cis-$Pt^{II}$($NH_3$)(c-$C_7H_{11}NH_2$)$NO_3$ filtrate and stirring the mixture for 3 hours forming a yellow $Pt^{II}$($NH_3$)($C_7H_{11}N$)$Cl_2$ precipitate; o) evaporating the mixture to approximately 2 mL under reduced pressure and filtering yellow $Pt^{II}$($NH_3$)($C_7H_{11}N$)$Cl_2$ precipitate; p) washing the yellow $Pt^{II}$($NH_3$)($C_7H_{11}N$)$Cl_2$ precipitate with water and acetone, and drying the washed yellow $Pt^{II}$($NH_3$)($C_7H_{11}N$)$Cl_2$ precipitate in vacuo.

Other embodiments include, a method of making ammine/piperidine-dichloro-platinum(II) comprising: a) dissolving 5.5 mmol of K[$Pt(NH_3)Cl_3$] in 50 ML of water; b) adding 55 mmol of KI in 100 mL of water forming a brown solution and stirring for 20 minutes; c) adding 55 mmol of Piperidine in 10 mL of water dropwise to the brown solution until a golden yellow $Pt(NH_3)(C_5H_{11}N)I_2$ precipitate is formed and stirring for another hour; d) filtering the golden yellow $Pt(NH_3)(C_5H_{11}N)I_2$ precipitate and washing with acetone; e) drying in vacuo the washed golden yellow $Pt(NH_3)(C_5H_{11}N)I_2$ precipitate; f) suspending 4.24 mmol of $Pt(NH_3)(C_5H_{11}N)I_2$ in 100 ml of water; g) adding 8.48 mmol of $AgNO_3$ in 100 mL of water and stirring for 24 hours in the dark, at room temperature; h) filtering an AgI precipitate; i) evaporating the AgI filtrate to 50 mL; j) adding a 1:1 HCl solution dropwise while stirring forming a bright yellow $Pt(NH_3)(C_5H_{11}N)Cl_2$ compound; and k) filtering the bright yellow $Pt(NH_3)(C_5H_{11}N)Cl_2$ compound and re-crystallizing the bright yellow $Pt(NH_3)(C_5H_{11}N)Cl_2$ compound in hot water and drying the bright yellow $Pt(NH_3)(C_5H_{11}N)Cl_2$ crystals under vacuum.

Still other embodiments of the invention include, a method of making ammine/hexamethyleneimine-dichloro-platinum(II) comprising: a) dissolving 5.5 mmol of $K[Pt(NH_3)Cl_3]$ in 50 mL of water; b) adding 55 mmol of KI in 100 mL of water forming a brown solution and stirring for 20 minutes; c) adding 55 mmol of hexamethylenimine in 10 mL of water dropwise to the brown solution until a golden yellow $Pt(NH_3)(C_6H_{13}N)I_2$ precipitate is formed and stirring for an hour; d) filtering the golden yellow $Pt(NH_3)(C_6H_{13}N)I_2$ precipitate and washing with acetone; e) drying in vacuo the washed golden yellow $Pt(NH_3)(C_6H_{13}N)I_2$ precipitate; f) suspending 4.24 mmol of $Pt(NH_3)(C_6H_{13}N)I_2$ in 100 ml of water; g) adding 8.48 mmol of $AgNO_3$ in 100 mL of water and stirring for 24 hours in the dark, at room temperature; h) filtering an AgI precipitate; i) evaporating the AgI filtrate to 50 mL; j) adding a 1:1 HCl solution dropwise while stirring forming a bright yellow $Pt(NH_3)(C_6H_{13}N)Cl_2$ compound; and k) filtering the bright yellow $Pt(NH_3)(C_6H_{13}N)Cl_2$ compound and re-crystallizing the bright yellow $Pt(NH_3)(C_6H_{13}N)Cl_2$ compound in hot water and drying the bright yellow $Pt(NH_3)(C_6H_{13}N)Cl_2$ crystals under vacuum.

Additional embodiments include, a method of making ammine/hexamethyleneimine-tetrachloro-platinum(IV) comprising: a) adding 10 milliliters of $H_2O_2$ to a suspension of 2.61 mmol $Pt^{II}(NH_3)(C_6H_{13}N)Cl_2$ in 200 mL of water, stirring for 15 hours, filtering the solution, concentrating to a minimum volume; b) precipitating with acetone forming a yellow $(Pt^{IV}(NH_3)(C_6H_{13}N)trans-(OH)_2Cl_2)$ product; c) drying the yellow $(Pt^{IV}(NH_3)(C_6H_{13}N)trans-(OH)_2Cl_2)$ in vacuo; d) dissolving the yellow 1.64 mmol of $Pt^{IV}(NH_3)(C_6H_{13}N)trans-(OH)_2Cl_2$ (0.65 g; 1.64 mmol) in 100 mL of water; e) adding 20 mL of concentrated HCl and stirring for 24 hours at room temperature forming a clear yellow solution; f) filtering the clear yellow solution, concentrating the clear yellow solution to a minimum volume to form a yellow crystalline $Pt^{IV}(NH_3)(C_6H_{13}N)Cl_4$; and g) filtering, washing the yellow crystalline $Pt^{IV}(NH_3)(C_6H_{13}N)Cl_4$ with water, and drying under a vacuum.

All amounts as disclosed herein are approximate and may vary by about 5 to about 10, about 15 to about 20 percent or more. In other embodiments of the present invention, the amount may vary by about 1, 2, 3, 4, 5, 6, 7, 8, 9, 10, 11, 12, 13, 14, 15, 16, 17, 18, 19, 20 or more millimolars. The amounts as disclosed herein may also vary by about 5 to about 10, about 15 to about 20, about 25 to about 30 or more millitters.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Resistance to platinum complexes may be overcome by the enhanced and/or selective antitumor activity of a specific platinum complex(es) alone or in combination with negative modulators of GSH. In certain embodiments, a negative modulator of GSH may be an inhibitor of GSH synthesis, which includes, but is not limited to, L-buthionine-SR-sulfoximine (BSO), which may include one to more isomers of BSO. Embodiments of the invention result in an increased activity against cisplatin-resistant cells that is greater than the activity against cisplatin-sensitive cells. The combination of a specific platinum analog and an inhibitor of GSH synthesis or activity (e.g., BSO) may be used against refractory cancers, and is independent of the p53 status of the target cells.

Figure 1:
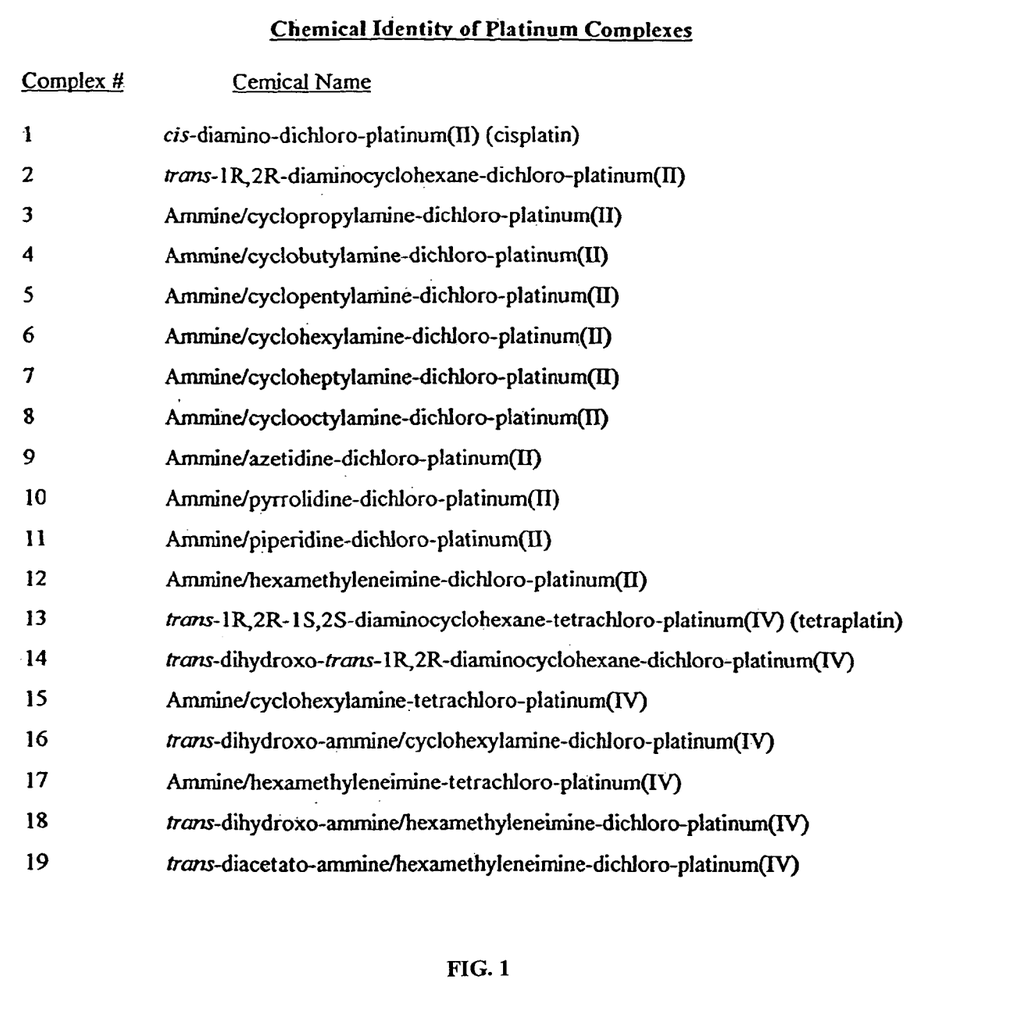
FIG. 1. List of the chemical identity of exemplary platinum complexes.
Figure 2:
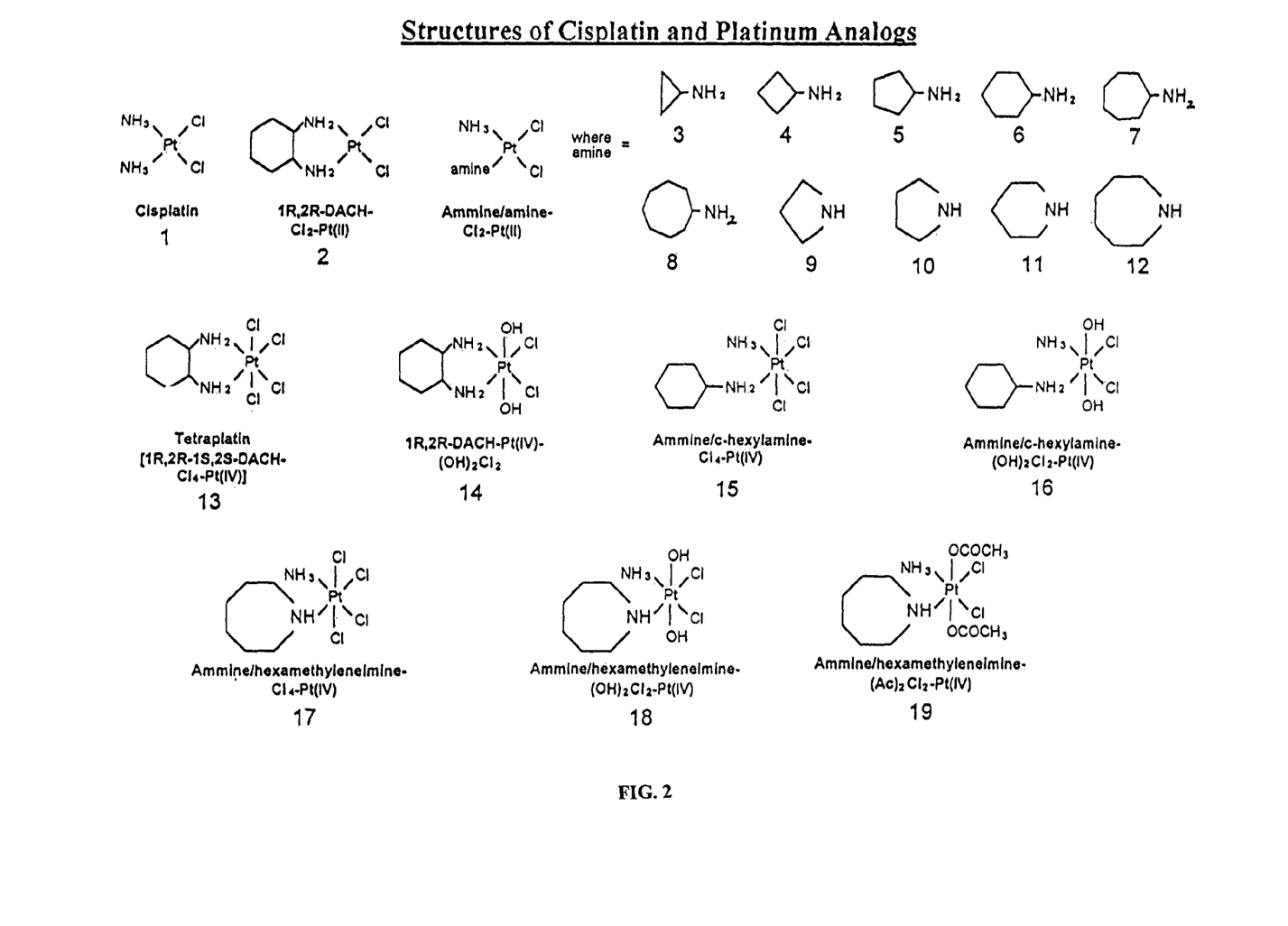
FIG. 2. Schematic of the structures representing the chemicals described in the application and provided in FIG. 1.

The increase in antitumor activity in combination with BSO is usually under 2-fold for cisplatin, although isolated publications have demonstrated increases of up to 4-fold. Moreover, the increased activity of cisplatin is not selective, as both sensitive and resistant cells respond equally well. Other analogs of cisplatin have been demonstrated to behave in a similar manner. Platinum complexes referred to in the present disclosure are listed by complex number, chemical name, and chemical structures provided in FIG. 1 and FIG. 2.

The inventors have identified specific platinum complexes which when administered in combination with an inhibitor of GSH synthesis (e.g. BSO), show (1) substantially greater enhancement in antitumor activity, and (2) selectivity for cisplatin-resistant cells. Thus, in isogenic pairs of sensitive and resistant tumor models, the activity of specific analogs is much greater against resistant cells than against sensitive cells.

The present invention includes formulations and methods for the treatment of cancer and other hyperproliferative diseases using pharmaceutical compositions including platinum complexes and/or a biologic response modifying agent, such agents enhance the activity of an antitumor compound or enhances the sensitivity of a tumor cell to an antitumor compound. In certain embodiments, the platinum complexes may include one or more of ammine/cycloheptylamine-dichloro-platinum(II) (complex No. 7), ammine/piperidine-dichloro-platinum(II) (complex No. 11), ammine/hexamethyleneimine-dichloro-platinum(II) (complex No. 12), and ammine/hexamethyleneimine-tetrachloro-platinum(IV) (complex No. 17), which are represented by the chemical structures described herein.

I. Platinum Complexes

Cisplatin is a clinically very important anticancer/antitumor metal-based drug which coordinates to DNA and distorts its double-helical conformation (Rosenberg, 1999; O'Dwyer et al., 1999; Reedijk, 1996; Lepre and Lippard, 1990; Johnson et al., 1989). The anticancer effects of cisplatin are associated with the capability of these distortions to terminate DNA polymerase (Comess et al., 1992) and to induce apoptosis (Eastman, 1999). In addition, these distortions attract various damaged DNA-binding proteins and the binding of these proteins has been postulated to mediate the antitumor properties of cisplatin (Jamieson and Lippard, 1999; Zamble and Lippard, 1999). The compounds of the invention have antitumor activity comparable to or better than cisplatin and show little or no cross resistance, i.e., resistance to cisplatin does not correspond to resistance to the compounds of the invention. Such compounds are typically more effective than cisplatin against cisplatin-resistant cell lines.

Certain embodiments of the invention may include ammine/cycloheptylamine-dichloro-platinum(II), complex #7, a compound represented by the structure:

Structural Formula I and salts thereof

Some embodiments of the invention may include ammine/piperidine-dichloro-platinum(II), complex #11, a compound represented by the structure:

Structural Formula II and salts thereof.

Various embodiments of the invention may include ammine/hexamethyleneimine-dichloro-platinum(III), complex #12, a compound represented by the structure:

Structural Formula III and salts thereof.

Other embodiments of the invention may include ammine/hexamethyleneimine-tetrachloro-platinum(IV), complex #17, a compound represented by the structure:

Structural Formula IV and salts thereof.

In various embodiments of the invention, a platinum complex of ammine/cycloheptylamine-dichloro-platinum (II), ammine/piperidine-dichloro-platinum(II), ammine/hexamethyleneimine-dichloro-platinum(II), and/or ammine/hexamethyleneimine-tetrachloro-platinum(IV) is administered to a patient in need of treatment for a cancerous or hyperproliferative condition. The complexes may be administered alone or in combination with an inhibitor or inhibitors of GSH synthesis or activity. In certain embodiments, an inhibitor or inhibitors of GSH synthesis is administered before, after or at the same approximate time as ammine/cycloheptylamine-dichloro-platinum(II), ammine/piperidine-dichloro-platinum(II), ammine/hexamethyleneimine-dichloro-platinum(II), ammine/hexamethyleneimine-tetrachloro-platinum(IV) or a combination thereof. In various embodiments, a patient or subject has a tumor, cancer or hyperproliferative cells that are resistant to cisplatin, carboplatin or other therapies. In some embodiments, the platinum complex is selective for cells resistant to cisplatin, carboplatin or other therapies and agents.

II. Inhibitors of GSH Synthesis or Activity

Glutathione (L-glutamyl-L-cysteine-glycine; GSH) is found in almost all cells in relatively high concentrations (1 to 10 mM) (Meister and Anderson, 1983; Anderson and Meister, 1983). GSH has a number of cellular functions. It is an effective intracellular reductant. It also functions in the catalysis, metabolism, transport and protection of cells against foreign compounds, free radicals and reactive oxygen compounds. GSH is an active participant in reactions that destroy $H_2O_2$ and organic peroxides.

GSH is synthesized intracellularly by consecutive actions of γ-glutamylcysteine synthetase (reaction 1) and GSH synthetase (reaction 2) (Anderson, 1997):

L-glutamate+L-cysteine+ATP⇌L-γ-glutamyl-L-cysteine+ADP+Pi (Meister and Anderson, 1983)

L-γ-glutamyl-L-cysteine+glycine+ATP⇌glutathione+ADP+Pi (Anderson and Meister; 1983)

The synthesis of GSH is limited by the availability of substrates, the limiting substrate is typically cysteine. γ-Glutamylcysteine synthetase is non-allosterically, feedback inhibited by GSH (Richman and Meister, 1973). Glutathione is homeostatically controlled, both inside and outside of the cell. Enzyme systems synthesize it, utilize it, and regenerate it in what is known as the γ-glutamyl cycle.

In various embodiments of the invention, a combination therapy of a platinum complex and an inhibitor of GSH synthesis may be used as an antitumor formulation or composition and in antitumor methods or treatments.

A. Inhibitors of γ-glutamylcysteine Synthetase

BSO was found to be a specific inhibitor of γ-glutamylcysteine synthetase (Griffith and Meister, 1979, incorporated herein by reference). γ-Glutamylcysteine synthetase catalyzes the reaction of L-glutamate with MgATP to form g-glutamyl phosphate as an enzyme bound intermediate (Griffith, 1982 and Campbell et al., 1991, each of which is incorporated herein by reference). In particular, S-butyl homocysteine sulfoximine inhibits γ-Glutamylcysteine synthetase about 20 times more effectively than did prothionine sulfoximine at least 100 times more effectively than methionine sulfoximine.

B. Inhibitors of Glutathione Transferase (GST)

Agents that inhibit the conjugation of GSH to other compounds may also be used in combination with one or more platinum complexes of the invention. Various compounds are classified as GST inhibitors. GST inhibitors include but are not limited to peptides, peptide mimetics, small molecules, and the like. Tricyclic antidepressants such as amitriptyline, doxepin, cycloheptadiene, and derivatives thereof are known to inhibit the activity of various GST enzymes. Exemplary inhibitors and methods are described in Tew et al., 1997; Baranczyk et al., 2001; Burg et al., 2002; Tew, 1994; and Kunze, 1996.

Kuzne et al. (1996) describe phosphono-analogues of glutathione containing the O=P(OR)$_2$ moiety in place of the cysteinyl residue CH$_2$SH were prepared by solution phase peptide synthesis. The inhibition of the glutathione conjugation of 1-chloro-2,4-dinitrobenzene by human placental glutathione S-transferase was studied by determining the IC50 values of the new glutathione analogues. The IC50 values were 291 microM, 139 microM, 64 microM, and 21 microM for the dimethyl, diethyl, diisopropyl, and di-n-butyl esters, respectively. The results clearly show that the formal substitution of the glutathione thiol function by phosphonic acid esters leads to a new class of glutathione S-transferase inhibitors.

Tew et al. (1997) describe the function of ethacrynic acid (EA) and Terrapin 199 (TER 199) in the inhibition of GST. EA, an inhibitor of all classes of GST isozymes, has been used clinically in combination with thiotepa. TER 199, a glutathione analog-based GTS inihibitor, has been modeled speficically to inhibit GST pi, an enzyme which is commonly found at high levels in human tumor biopsies. Furthermore, a therapeutic strategy has been designed to take advantage of GST pi activation of a produg, TER 286.

Burg et al. (2002) described the synthesis of a series of peptidomimetic glutathione analogues stabilized against peptidase mediated breakdown. The peptide bonds in GSH were replaced by isosteres, such as the 'reduced' amide (which was prepared using a novel method), N-methylamide, urethane, and methylene linkages. The in vitro evaluation of the compounds focused on GST inhibition and stability towards gamma-glutamyl-transpeptidase (gammaGT), the main enzyme involved in GSH breakdown. The compounds were conjugated to the model electrophile ethacrynic acid (EA) to resemble GS-EA, an efficient GST inhibitor. All new GSH-analogues were shown to inhibit rat liver cytosolic GSTs. Furthermore, peptidomimeric changes of the γ-glutamyl-cysteine amide bond greatly improved stability towards γGT.

III. Combination Therapy

Current treatment for many types of cancer, in particular treatment of gynecologic cancers, is mainly surgery, radiation, or chemotherapies. The present invention includes methods comprising the administration of one or more platinum complexes selected from the group consisting of ammine/cycloheptylamine-dichloro-platinum(II), ammine/piperidine-dichloro-platinum(II), ammine/hexamethyleneimine-dichloro-platinum(II), and ammine/hexamethyleneimine-tetrachloro-platinum(IV). The platinum complex may be administered in combination with inhibitors of glutathione synthesis or activity to patients diagnosed with various cancers and in particular cancers that have demonstrated a resistance to treatment with other platinum based therapies. Additionally, these formulations or compositions and methods may be administered in combination with other conventional and developing therapies.

In many therapies, it will be advantageous to provide more than one functional therapeutic or agent. Such "combined" therapies may have particular import in treating multiple aspects of a condition, disease, or other abnormal physiology, such as resistance to one or more conventional therapies. For example, treating multidrug resistant (MDR) cancers. Thus, one aspect of the present invention utilizes administration of one or more platinum complexes to an appropriate site in a tissue, organ or organism for treatment of diseases, while a second therapy providing therapeutic and/or enhancing or sensitizing effects is also provided.

A sensitizing or enhancing treatment may precede or follow platinum complex treatment(s) by intervals ranging from seconds, minutes up to weeks. In embodiments where the other agent and platinum complexes are administered separately to the site or subject of interest, one would generally ensure that a significant period of time did not expire between the time of each delivery, such that an agent and a platinum complex would still be able to exert an advantageously combined effect on a treatment site. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either agent will be desired. Various combinations may be employed, where the platinum complex (ammine/cycloheptylamine-dichloro-platinum(II), ammine/piperidine-dichloro-platinum(II), ammine/hexamethyleneimine-dichloro-platinum(II), ammine/hexamethyleneimine-tetrachloro-platinum(IV), or a combination thereof) is "A" and the other agent is "B", as exemplified below:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

The other agent may be a therapeutic, enhancing and/or sensitizing agent, such as an inhibitor of GSH synthesis or other cancer therapeutics.

Other combinations are contemplated. For example, in the context of the present invention, it is contemplated that platinum complexes of the present invention could be used in conjunction with other anti-cancer agents, including chemo- or radiotherapeutic intervention. To kill cells, inhibit cell growth, inhibit metastasis, inhibit angiogenesis or otherwise reverse or reduce the malignant phenotype of tumor cells, using the methods and formulations/compositions of the present invention, one would generally contact a "target" cell with a platinum complex, as described herein and at least one other agent, such as a GSH synthesis inhibitor; these formulations/compositions would be provided in a combined amount effective achieve these goals. This process may involve exposing the site(s) targeted for treatment with the platinum complexes and an other agent(s) or factor(s) at the same time. This may be achieved by administering or providing a single composition or pharmacological formulation that includes both agents, or by administering two distinct compositions or formulations, at the same or different time, wherein one composition includes a platinum complex(es) and another includes the sensitizing or enhancing agent. In certain embodiments, the compositions and methods of the invention may be used after or before standard cisplatin therapy.

In other embodiments an agent suitable for use in a combined therapy with the platinum complexes of the invention are any chemical compound or treatment method with therapeutic activity. For example, an "anticancer agent" refers to an agent with anticancer activity. These compounds or methods include other alkylating agents, topisomerase I inhibitors, topoisomerase II inhibitors, RNA/DNA antimetabolites, DNA antimetabolites, antimitotic agents, as well as DNA damaging agents, which induce DNA damage when applied to a cell.

Examples of alkylating agents include, inter alia, chlorambucil, cis-platinum, cyclodisone, flurodopan, methyl CCNU, piperazinedione, teroxirone. Topisomerase I inhibitors encompass compounds such as camptothecin and camptothecin derivatives, as well as morpholinodoxorubicin. Doxorubicin, pyrazoloacridine, mitoxantrone, and rubidazone are illustrations of topoisomerase II inhibitors. RNA/DNA antimetabolites include L-alanosine, 5-fluoraouracil, aminopterin derivatives, methotrexate, and pyrazoflirin; while the DNA antimetabolite group encompasses, for example, ara-C, guanozole, hydroxyurea, thiopurine. Typical antimitotic agents are colchicine, rhizoxin, taxol, and vinblastine sulfate. Other agents and factors include radiation and waves that induce DNA damage such as, γ-irradiation, X-rays, UV-irradiation, microwaves, electronic emissions, and the like. A variety of anti-cancer agents, also described as "chemotherapeutic agents," function to induce DNA damage, all of which are intended to be of use in the combined treatment methods disclosed herein. Chemotherapeutic agents contemplated to be of use, include, e.g., adriamycin, bleomycin, 5-fluorouracil (5FU), etoposide (VP-16), camptothecin, actinomycin-D, mitomycin C, cisplatin (CDDP), podophyllotoxin, verapamil, and even hydrogen peroxide. The invention also encompasses the use of a combination of one or more DNA damaging agents, whether radiation-based or actual compounds, such as the use of X-rays with cisplatin or the use of cisplatin with etoposide.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In addition to combining platinum complex therapies with sensitizing, or chemo- and radiotherapies, it also is contemplated that combination with gene therapies will be advantageous. For example, using a combination of p53, p16, p21, Rb, APC, DCC, NF-1, NF-2, BCRA2, p16, FHIT, WT-1, MEN-I, MEN-II, BRCA1, VHL, FCC, or MCC, or antisense versions of the oncogenes ras, myc, neu, raf, erb, src, fms, jun, trk, ret, gsp, hst, bcl, abl, or any of the genes mentioned above are included within the scope of the invention.

IV. Disease States

The present invention deals with the treatment of disease states that involve hyperproliferative disorders including benign and malignant neoplasias. Such disorders include hematological malignancies, restenosis, cancer, multi-drug resistant cancer, primary, psoriasis, inflammatory bowel disease, rheumatoid arthritis, osteoarthritis and metastatic tumors.

In particular, the present invention is directed at the treatment of human cancers including cancers of the prostate, lung, brain, skin, liver, breast, lymphoid system, stomach, testicular, ovarian, pancreatic, bone, bone marrow, head and neck, cervical, esophagus, eye, gall bladder, kidney, adrenal glands, heart, colon, rectum and blood, in particular those cancers that have developed or may develop resistance to conventional chemotherapies. Other diseases that may be treated with formulations/compositions or methods of the invention also may include renal cell carcinomas; viral infections such as, hepatitis C (Garini et al., 2001), HIV-1 (Hatzakis et al., 2001); Erdheim-Chester disease (Esmali et al., 2001), thrombocytopenic purpura (Dikici et al., 2001), marburg hemorrhagic fever (Kolokol'tsov et al., 2001) In certain embodiments, methods and formulations/compositions are used to treat a subject with ovarian cancer.

V. Synthesis of Platinum Complexes

A. Preparation of Ammine/cyclopentylamine-dichloroplatinum(II) cis-$Pt^{II}(NH_3)(c-C_5H_9NH_2)Cl_2$ (compound #5)

An aqueous solution of $K_2PtCl_4$ (8.30 g; 20 mmol) was treated with KI (33.2 g; 200 mmol) and stirred for 10 minutes at room temperature. Two equivalents of cyclopentylamine were added dropwise to the $K_2PtI_4$ solution. Upon stirring for 30 minutes a yellow precipitate (cis-$Pt^{II}(c-C_5H_9NH_2)_2I_2$) was formed. The yellow precipitate was filtered and washed extensively with water. The precipitate was recrystallized from a $DMF/H_2O$ mixture. After washing with water, methanol, and ethyl ether, the crystallized product (cis-$Pt^{II}(c-C_5H_9NH_2)_2I_2$) was dried in vacuo.

One hundred fifty milliliters (mL) of ethanol was added to a suspension of cis-$Pt^{II}(c-C_5H_9NH_2)_2I_2$ (6.19 g; 10 mmol) in 50 mL of 60-70% $HClO_4$. In the course of the reaction samples were taken for analysis by $^{195}Pt$ NMR spectroscopy. At the end of 4 days of stirring at room temperature a brown precipitate ([$Pt^{II}(c-C_5H_9NH_2)I_2]_2$) was filtered, washed with water, and dried in vacuo.

[$Pt^{II}(c-C_5H_9NH_2)I_2]_2$ (5.25 g; 5 mmol) was mixed with 5 mL of 1.5 M $NH_4OH$ in 25 mL of water. The mixture was stirred at room temperature overnight. Again the completeness of the reaction was monitored by $^{195}Pt$ NMR spectroscopy. A yellow precipitate (cis-$Pt^{II}(NH_3)(c-C_5H_9NH_2)I_2$) was filtered, washed with water, and dried in vacuo.

cis-$Pt^{II}(NH_3)(c-C_5H_9NH_2)I_2$ (2.20 g; 4 mmol) was mixed with $AgNO_3$ (1.25 g; 7.4 mmol) in 200 mL of water and stirred overnight in the dark. After the removal of AgI by filtration through celite, 10 mL of concentrated HCl was added to the filtrate. The mixture was allowed to stir for 3 hours and then evaporated to approximately 2 mL under reduced pressure. A yellow precipitate (cis-$Pt^{II}(NH_3)(c-C_5H_9NH_2)Cl_2$) was filtered, washed with water and acetone, and dried in vacuo.

B. Preparation of Ammine/cycloheptylamine-dichloroplatinum(II) [$Pt^{II}(NH_3)(C_7H_{11}N)Cl_2$] (compound #7)

An aqueous solution of $K_2PtCl_4$ (8.30 g; 20 mmol) was treated with KI (33.2 g; 200 mmol) and stirred for 10 minutes at room temperature. Two equivalents of cycloheptylamine were added dropwise to the resulting $K_2PtI_4$ solution. Upon stirring for 30 minutes yellow precipitate (cis- $Pt^{II}(c\text{-}C_7H_{11}NH_2)_2I_2)$ was formed. The yellow precipitate was filtered and washed extensively with water. The precipitate was recrystallized from a DMF/H$_2$O mixture. After washing with water, methanol, and ethyl ether, the product (cis-$Pt^{II}(c\text{-}C_7H_{11}NH_2)_2I_2$) was dried in vacuo.

One hundred fifty milliliters (mL) of ethanol was added to a suspension of cis-$Pt^{II}(c\text{-}C_7H_{11}NH_2)_2I_2$ (10 mmol) in 50 mL of 60-70% HClO$_4$. In the course of reaction samples were taken for analysis by $^{195}$Pt NMR spectroscopy. At the end of 4 days of stirring at room temperature a brown precipitate ($[Pt^{II}(c\text{-}C_7H_{11}NH_2)I_2]_2$) was filtered, washed with water, and dried in vacuo.

$[Pt^{II}(c\text{-}C_7H_{11}NH_2)I_2]_2$ (5 mmol) was mixed with 5 mL of 1.5M NH$_4$OH in 25 mL of water. The mixture was stirred at room temperature overnight. Again the completeness of the reaction was monitored by $^{195}$Pt NMR spectroscopy. A yellow precipitate (cis-$Pt^{II}(NH_3)(c\text{-}C_7H_{11}NH_2)I_2$) was filtered, washed with water, and dried in vacuo.

cis-$Pt^{II}(NH_3)(c\text{-}C_7H_{11}NH_2)I_2$ (4 mmol) was mixed with AgNO$_3$ (1.25 g; 7.4 mmol) in 200 mL of water and stirred overnight in the dark. After the removal of AgI by filtration through celite, 10 mL of concentrated HCl was added to the filtrate, the mixture was allowed to stir for 3 hours and then evaporated to approximately 2 mL under reduced pressure. The yellow precipitate ($Pt^{II}(NH_3)(C_7H_{11}N)Cl_2$) was filtered, washed with water and acetone, and dried in vacuo.

C. Preparation of Ammine/piperidine-dichloro-platinum (II) [$Pt^{II}(NH_3)(C_5H_{11}N)Cl_2$] (compound #11)

Cosa salt K[Pt(NH$_3$)Cl$_3$] (1.98 g; 5.5 mmol) was dissolved in 50 mL of water. KI (9.19 g; 55 mmol) in 100 mL of water was added to the Cosa salt solution. A brown solution was formed upon the addition the KI solution. The reaction mixture was stirred for 20 minutes. Piperidine (55 mmol) in 10 mL of water was added dropwise to the reaction mixture until a golden yellow precipitate ([Pt(NH$_3$)(C$_5$H$_{11}$N)I$_2$]) was formed. The reaction mixture was kept stirring for another hour. The precipitate was filtered, washed with acetone, and dried in vacuo. A golden yellow compound [Pt(NH$_3$)(C$_5$H$_{11}$N)I$_2$] was obtained. [Pt(NH$_3$)(C$_5$H$_{11}$N)I$_2$] (2.39 g, 4.24 mmol) was suspended in 100 ml of water. AgNO$_3$ (1.44 g; 8.48 mmol) in 100 mL was added. The reaction mixture stirred for 24 hours in the dark, at room temperature. AgI precipitate was filtered, and the filtrate was evaporated to 50 mL. HCl (1:1) was added dropwise while stirring. A bright yellow compound [Pt(NH$_3$)(C$_5$H$_{11}$N)Cl$_2$] was obtained. It was filtered and re-crystallized with hot water and dried under vacuum.

D. Preparation of Ammine/hexamethyleneimine-dichloro-platinum(II) cis-$Pt^{II}(NH_3)(C_6H_{13}N)Cl_2$ (compound #12)

Cosa salt K[Pt(NH$_3$)Cl$_3$] (1.98 g; 5.5 mmol) was dissolved in 50 mL of water. KI (9.19 g; 55 mmol) in 100 mL of water was added. A brown solution was formed. The reaction mixture was stirred for 20 minutes. Hexamethylenimine (55 mmol) in 10 mL of water was added dropwise to the reaction mixture until a golden yellow precipitate (Pt(NH$_3$)(C$_6$H$_{13}$N)I$_2$) was formed. The reaction mixture was kept stirring for another hour. The precipitate was filtered, washed with acetone, and dried in vacuum. A golden yellow compound (Pt(NH$_3$)(C$_6$H$_{13}$N)I$_2$) was obtained. Pt(NH$_3$)(C$_6$H$_{13}$N)I$_2$ (4.24 mmol) was suspended in 100 ml of water. AgNO$_3$ (1.44 g; 8.48 mmol) in 100 mL was added. The reaction mixture stirred for 24 hours in the dark, at room temperature. An AgI precipitate was filtered, and the filtrate was evaporated to 50 mL. HCl (1:1) was added dropwise while stirring. A bright yellow compound [Pt(NH$_3$) (C$_6$H$_{13}$N)Cl$_2$] was obtained. It was filtered and re-crystallized with hot water and dried under vacuum.

E. Preparation of Ammine/hexamethyleneimine-tetra-chloro-platinum(IV) $Pt^{IV}(NH_3)(C_6H_{13}N)Cl_4$ (Compound #17)

Ten milliliters of H$_2$O$_2$ was added to a suspension of Pt$_{II}$(NH$_3$)(C$_6$H$_{13}$N)Cl$_2$ (1.0 g; 2.61 mmol) in 200 mL of water and was stirred for 15 hours. The solution was filtered, concentrated to a minimum volume, and precipitated with acetone. A yellow product ($Pt^{IV}(NH_3)(C_6H_{13}N)$trans-(OH)$_2$Cl$_2$) was obtained. ($Pt^{IV}(NH_3)(C_6H_{13}N)$trans-(H)$_2$Cl$_2$) was dried in vacuo. $Pt^{IV}(NH_3)(C_6H_{13}N)$trans-(OH)$_2$Cl$_2$ (0.650 g; 1.64 mmol) was dissolved in 100 mL of water and 20 mL of concentrated HCl was added. The reaction mixture was kept stirring for 24 hours at room temperature. A clear yellow solution was obtained. It was filtered, concentrated to a minimum volume to get a yellow crystalline solid ($Pt^{IV}(NH_3)(C_6H_{13}N)Cl_4$). It was filtered, washed with water, and dried under vacuum.

VI. Pharmaceutical Preparations

Pharmaceutical formulations/compositions of the present invention comprise an effective amount of platinum complex, as described herein. In various other embodiments, combinations of a platinum complex and a biological modifier agent(s) are dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contain a platinum complex of the invention and/or in combination with an inhibitor of glutathione synthesis or additional active ingredient will be known to those of skill in the art in light of the present disclosure. Examples and guidance for pharmaceutical composition and methods known to one skilled in the art may be found in Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The compositions comprising the platinum complexes of the invention or a combination of the platinum complexes of the invention and inhibitors of glutathione synthesis may comprise different types of carriers depending on whether it is to be administered in a solid or liquid form, and whether it needs to be sterile for such routes of administration as injection. The present invention can be administered intravenously, intradermally, intraarterially, intramuscularly, intraperitoneally, subcutaneously, orally, by injection, by infusion, by continuous infusion, in lipid compositions (e.g., liposomes), or by other methods or any combination of the foregoing as would be known to one of ordinary skill in the art (see, for example, Remington's Pharmaceutical Sciences, 18th Ed. Mack Printing Company, 1990, incorporated herein by reference). Compositions contemplated or encompassed by the instant invention include conventional pharmaceutical formulations, including intravenously administered formulation(s) or by any other method or any combination of the foregoing as would be known to one of ordinary skill in the art (see for example, Remington's Pharmaceutical Sciences, 18th Ed., Mack Printing Company, 1990, incorporated herein by reference).

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. Also, dosage may be approximately 1, 2, 3, 4, 5, 6, 7, 8, 9, 10, 11, 12, 13, 14, 15, 16, 17, 18, 19, 20, 30, 40, 50, 60, 70, 80, 90, 100 or more mg/m$^2$ including all doses there between.

In various embodiments the concentration of a platinum complex in a pharmaceutical formulation or composition may be in the approximate range of 0.1 µM, 0.5 µM, 1 µM, 2 µM, 3 µM, 4 µM, 5 µM, 6 µM, 7 µM, 8 µM, 9 µM, 10 µM, 25 µM, 50 µM, 0.1 mM, 0.5 mM, 1 mM to 10 µM, 11 µM, 12 µM, 13 µM, 14 µM, 15 µM, 16 µM, 17 µM, 18 µM, 19 µM, 20 µM, 50 µM, 0.1 mM, 1 mM, 2 mM, 3 mM, 4 mM, 5 mM, 6 mM, 7 mM, 8 mM, 9 mM, or 10 mM.

In any case, the formulation or composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The therapeutic compositions of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In certain embodiments, the therapeutic compositions of the present invention are typically prepared for administration by such routes as intravenous injection. In these embodiments, the composition may comprise, for example, solutions, suspensions, emulsions, or combinations thereof.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsions, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as a solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Experimental Procedure

The ovarian A2780 and 2008 cell lines are sensitive to cisplatin, while the corresponding 2780CP and 2008/C13* cell lines were selected for resistance following in vitro exposure to cisplatin. The SKOV-3 cell line was established from a patient who was resistant to cisplatin therapy and is considered a model of cisplatin resistance. The A2780 and 2780CP cells have wild-type p53 function, while SKOV-3 is devoid of p53 function. The p53 status for the 2008 and 2008/C131 cells is presently not known.

Procedure for Cytotoxic Evaluation. All cell lines are maintained in RPMI 1640 medium supplemented with 10% fetal bovine serum, 50 µg/ml penicillin, 50 µg/ml streptomycin, 100 µg/ml neomycin and 0.3 mg/ml L-glutamine. The ovarian lines also require 2 µg/ml insulin for maximal growth. Cells are grown as monolayers at 37° C. in a humidified atmosphere of 5% $CO_2$:95% air. Cytotoxicity is determined by a standard MTT assay. Briefly, the exponentially-growing cells are trypsinized to dislodge them before use. After diluting the tumor cells to appropriate concentrations (2,000-30,000 cells/ml), 100 µl aliquots of the cell suspensions are added to each well of a 96-well microtiter plate. The cells are allowed to attach overnight, and then exposed for 24 hr to BSO at a concentration that is equal to or less than maximally tolerated concentration (MTC). At 22 hr after addition of BSO, the platinum complex is added, and 2 hr later the cells are washed and reincubated. After another 5 days, when control cells are in an exponential phase of growth, 50 µl of an MTT solution (3 mg/ml) is added to each well. Following a 3-hr incubation, the medium is removed and replaced by 50 µl of 100% DMSO to dissolve MTT formazan crystals. Plates are agitated on a plate shaker for 5 min, and absorbances are measured at 570 nm in a multiwell scanning spectrophotometer.

$IC_{50}$ values, defined as the drug concentration (µM) inhibiting cell growth by 50% compared to control wells, are determined by fitting a sigmoidal curve to the data using a computer program. Resistance factor is calculated as a ratio of the $IC_{50}$ against resistant cell line to the $IC_{50}$ against parent cell line. The dose modification factor (DMF) is derived from a ratio of $IC_{50}$ without BSO to that with BSO.

Example 2

Evaluation of Antitumor Activity

The inventors have identified specific platinum complexes which when administered in combination with an inhibitor of GSH synthesis (e.g., BSO), show (1) substantially greater enhancement in antitumor activity, and (2) selectivity for cisplatin-resistant cells. The data demonstrates that in isogenic pairs of sensitive and resistant tumor models, the activity of specific analogs is much greater against resistant cells than against sensitive cells (Table 1).

TABLE 1

Cytotoxicity of Cisplatin and Analogs Against Human A2780 and 2780CP Cell Lines in Absence or Presence of BSO

| Platinum analog Complex #. | $IC_{50}$ (µM) vs. A2780 | | $IC_{50}$ (µM) vs. 2780CP | | |
|---|---|---|---|---|---|
| | Control (Without BSO) | +10 µM BSO (MTC) | Control (Without BSO) | +10 µM BSO | +3 mM BSO (MTC) |
| 1 (Cisplatin) | 6.75 | 4.25 | 100.6 | 82.0 | 58.3 |
| 2 | 0.56 | 0.41 | 4.61 | 3.69 | 2.46 |
| 3 | 3.64 | 3.46 | 63.7 | 62.2 | 48.8 |
| 4 | 1.03 | 0.77 | 16.6 | 16.0 | 15.8 |
| 5 | 0.73 | 0.66 | 15.2 | 14.5 | 9.07 |
| 6 | 0.63 | 0.50 | 7.55 | 6.98 | 4.19 |
| 7 | 1.23 | 0.94 | 12.3 | 6.92 | 1.96 |
| 8 | 0.77 | 0.61 | 7.41 | 5.97 | 2.35 |
| 9 | 4.27 | 3.02 | 27.2 | 18.7 | 8.20 |

TABLE 1-continued

Cytotoxicity of Cisplatin and Analogs Against Human A2780 and 2780CP Cell Lines in Absence or Presence of BSO

| Platinum analog Complex #. | $IC_{50}$ (µM) vs. A2780 | | $IC_{50}$ (µM) vs. 2780CP | | |
|---|---|---|---|---|---|
| | Control (Without BSO) | +10 µM BSO (MTC) | Control (Without BSO) | +10 µM BSO | +3 mM BSO (MTC) |
| 10 | 4.08 | 2.90 | 37.2 | 28.2 | 17.2 |
| 11 | 2.33 | 1.66 | 12.2 | 4.00 | 0.90 |
| 12 | 2.34 | 1.56 | 11.3 | 3.45 | 1.03 |
| 13 (Tetraplatin) | 8.48 | 4.57 | 44.8 | 34.9 | 23.5 |
| 14 | 1.25 | 1.17 | 15.8 | 15.5 | 9.54 |
| 15 | 0.91 | 0.72 | 15.4 | 10.8 | 4.34 |
| 16 | 3.55 | 3.07 | 23.9 | 19.6 | 8.92 |
| 17 | 3.27 | 1.60 | 9.54 | Nd | 0.87 |

MTC = Maximal tolerated concentration of BSO.
nd = not determined.

It is suggested that increased levels of GSH may constitute a mechanism of cisplatin resistance and that GSH inactivates the platinum complex by reducing the amount of the antitumor agent available. More recently, GSH has been implicated in modulation of programmed cell death or apoptosis pathways. Increased levels of GSH may inhibit the apoptotic process and, thereby, increase resistance to antitumor therapy or treatment. Thus, the inventors determined whether, reduction in cellular levels of GSH with BSO or other compounds that inhibit the activity or synthesis of GSH, increased the antitumor activity of cisplatin and other platinum complexes or compounds.

Cisplatin and a number of platinum analogs when combined with BSO showed an increase in antitumor activity by a factor less than 2-fold in both sensitive and resistant models (Table 2). Specific analogs, such as complex Nos. 7, 11, 12, and 17 (ammine/cycloheptylamine-dichloro-platinum(II), ammine/piperidine-dichloro-platinum(II), ammine/hexamethyleneimine-dichloro-platinum(II), and ammine/hexamethyleneimine-tetrachloro-platinum(IV), respectively) increased activity 5 to 14-fold in GSH-depleted human 2780CP tumor cells. These analogs also demonstrate selectively greater effectiveness against these cisplatin-resistant cells than the corresponding A2780 cisplatin-sensitive cells. The resistance factor for these analogs was also substantially reduced as demonstrated in Table 3 below. In particular, complex nos. 11, 12 and 17) showed a resistance factor 0.39, 0.44 and 0.27 respectively (Table 3). This increased activity was seen in human tumor cell lines harboring either wild-type or null p53 (Tables 4-6) and was found to be independent of p53 status.

TABLE 2

Dose Modification Factor (DMF) for Cisplatin and Analogs in Combination with BSO in Human A2780 and 2780CP Cell Lines

| Platinum analog | DMF vs. A2780 | | DMF vs. 2780CP | | |
|---|---|---|---|---|---|
| | Control (Without BSO) | +10 µM BSO (MTC) | Control (Without BSO) | +10 µM BSO | +3 mM BSO (MTC) |
| 1 (Cisplatin) | 1.00 | 1.59 | 1.00 | 1.23 | 1.73 |
| 2 | 1.00 | 1.37 | 1.00 | 1.25 | 1.87 |
| 3 | 1.00 | 1.05 | 1.00 | 1.02 | 1.31 |
| 4 | 1.00 | 1.34 | 1.00 | 1.04 | 1.05 |
| 5 | 1.00 | 1.11 | 1.00 | 1.05 | 1.68 |

TABLE 2-continued

Dose Modification Factor (DMF) for Cisplatin and Analogs in Combination with BSO in Human A2780 and 2780CP Cell Lines

| | DMF vs. A2780 | | DMF vs. 2780CP | | |
|---|---|---|---|---|---|
| Platinum analog | Control (Without BSO) | +10 μM BSO (MTC) | Control (Without BSO) | +10 μM BSO | +3 mM BSO (MTC) |
| 6 | 1.00 | 1.26 | 1.00 | 1.08 | 1.80 |
| 7 | 1.00 | 1.31 | 1.00 | 1.78 | 6.28 |
| 8 | 1.00 | 1.26 | 1.00 | 1.24 | 3.15 |
| 9 | 1.00 | 1.41 | 1.00 | 1.45 | 3.32 |
| 10 | 1.00 | 1.41 | 1.00 | 1.32 | 2.16 |
| 11 | 1.00 | 1.40 | 1.00 | 3.05 | 13.6 |
| 12 | 1.00 | 1.50 | 1.00 | 3.28 | 11.0 |
| 13 (Tetraplatin) | 1.00 | 1.86 | 1.00 | 1.28 | 1.91 |
| 14 | 1.00 | 1.07 | 1.00 | 1.02 | 1.66 |
| 15 | 1.00 | 1.26 | 1.00 | 1.43 | 3.55 |
| 16 | 1.00 | 1.16 | 1.00 | 1.22 | 2.68 |
| 17 | 1.00 | 2.04 | 1.00 | nd | 11.0 |

DMF determined as the ratio of $IC_{50}$ in absence (control) of BSO to $IC_{50}$ in presence of BSO.
MTC = Maximal tolerated concentration of BSO
nd = not determined.

TABLE 3

Resistance Factor for Cisplatin and Analogs in the Human 2780CP Cell Line in Absence or Presence of BSO

| | Resistance Factor vs. 2780CP | | |
|---|---|---|---|
| Platinum analog | Control (Without BSO) | +10 μM BSO | +3 mM BSO (MTC) |
| 1 (Cisplatin) | 14.9 | 12.1 | 8.63 |
| 2 | 8.23 | 6.59 | 4.39 |
| 3 | 17.5 | 17.1 | 13.4 |
| 4 | 16.1 | 15.5 | 15.3 |
| 5 | 20.8 | 19.9 | 12.4 |
| 6 | 12.0 | 11.1 | 6.65 |
| 7 | 10.0 | 5.63 | 1.59 |
| 8 | 9.62 | 7.75 | 3.05 |
| 9 | 6.37 | 4.38 | 1.92 |
| 10 | 9.12 | 6.91 | 4.22 |
| 11 | 5.24 | 1.72 | 0.39 |
| 12 | 4.83 | 1.47 | 0.44 |
| 13 (Tetraplatin) | 5.28 | 4.12 | 2.77 |
| 14 | 12.6 | 12.4 | 7.63 |
| 15 | 16.9 | 11.9 | 4.77 |
| 16 | 6.73 | 5.52 | 2.51 |
| 17 | 2.92 | Nd | 0.27 |

Resistance factor was determined as the ratio of $IC_{50}$ in 2780CP cells with or without BSO to $IC_{50}$ in A2780 cells without BSO.
MTC = Maximal tolerated concentration of BSO.
nd = not determined

TABLE 4

Cytotoxicity of Cisplatin and Analogs Against Human Tumor Cell Lines in Absence or Presence of BSO

| | $IC_{50}$ of Cisplatin (μM) | | $IC_{50}$ of complex No. 12 | | $IC_{50}$ of complex No. 17 | | $IC_{50}$ of complex No. 18 | | $IC_{50}$ of complex No. 19 | |
|---|---|---|---|---|---|---|---|---|---|---|
| Cell Line | Control | +BSO (MTC) | Control | +BSO (MTC) | Control | +BSO (MTC) | Control | +BSO (MTC) | Control | +BSO (MTC) |
| A2780 | 6.75 | 4.25 | 2.34 | 1.56 | 3.27 | 1.60 | nd | nd | nd | nd |
| 2780CP | 100.6 | 58.3 | 11.3 | 1.03 | 9.54 | 0.87 | nd | nd | Nd | nd |
| 2008 | 1.42 | 0.77 | 3.71 | 0.82 | Nd | nd | nd | nd | Nd | nd |
| 2008/C13* | 20.8 | 10.4 | 11.8 | 0.77 | 11.8 | 0.41 | nd | nd | Nd | nd |
| SKOV-3 | 33.0 | 21.1 | 24.7 | 1.41 | 22.1 | 1.80 | 140.0 | 14.2 | 100.0 | 21.6 |

Cytotoxicity of platinum complexes determined in absence (control) or presence of BSO [maximal tolerated concentration (MTC) for all cell lines, except SKOV-3 for which a sub-MTC was used].
nd = not determined.

TABLE 5

Dose Modification Factor (DMF) for Cisplatin and Analogs in Human Tumor Cell Lines in Absence or Presence of BSO

| | DMF for Cisplatin | | DMF for complex No. 12 | | DMF for complex No. 17 | | DMF for complex No. 18 | | DMF for complex No. 19 | |
|---|---|---|---|---|---|---|---|---|---|---|
| Cell Line | Control | +BSO (MTC) | Control | +BSO (MTC) | Control | +BSO (MTC) | Control | +BSO (MTC) | Control | +BSO (MTC) |
| A2780 | 1.00 | 1.59 | 1.00 | 1.50 | 1.00 | 2.04 | nd | nd | Nd | Nd |
| 2780CP | 1.00 | 1.73 | 1.00 | 11.0 | 1.00 | 11.0 | nd | nd | Nd | Nd |
| 2008 | 1.00 | 1.84 | 1.00 | 4.52 | Nd | nd | nd | nd | Nd | Nd |
| 2008/C13* | 1.00 | 2.00 | 1.00 | 15.3 | 1.00 | 28.8 | nd | nd | Nd | Nd |
| SKOV-3 | 1.00 | 1.56 | 1.00 | 17.5 | 1.00 | 12.3 | 1.00 | 9.86 | 1.00 | 4.63 |

DMF determined as the ratio of $IC_{50}$ in absence (control) of BSO to $IC_{50}$ in presence of BSO (maximal tolerated concentration (MTC) of BSO used for all cell lines, except SKOV-3 for which a sub-MTC was used).
nd = not determined.

TABLE 6

Resistance Factor (RF) for Cisplatin and Analogs in Human Tumor Cell Lines in Absence or Presence of BSO

| Cell Line | RF for Cisplatin | | RF for complex No. 12 | | RF for complex No. 17 | | Rf for complex No. 18 | | RF for complex No. 19 | |
|---|---|---|---|---|---|---|---|---|---|---|
| | Control | +BSO (MTC) | Control | +BSO (MTC) | Control | +BSO (MTC) | Control | +BSO (MTC) | Control | +BSO (MTC) |
| A2780 | 1.00 | — | 1.00 | — | 1.00 | — | nd | | nd | — |
| 2780CP | 14.9 | 8.63 | 4.83 | 0.44 | 2.92 | 0.27 | nd | | Nd | nd |
| 2008 | 1.00 | — | 1.00 | — | Nd | — | nd | nd | Nd | — |
| 2008/C13* | 14.6 | 7.32 | 3.18 | 0.21 | Nd | Nd | nd | nd | Nd | nd |
| SKOV-3 | 23.2 | 14.9 | 6.66 | 0.38 | Nd | Nd | nd | nd | Nd | nd |

Resistance factor was determined either as (1) the ratio of $IC_{50}$ in 2780CP cells with or without BSO to $IC_{50}$ in A2780 cells without BSO, or (2) the ratio of $IC_{50}$ in 2008/C13* and SKOV-3 cell lines with or without BSO to $IC_{50}$ in 2008 cells without BSO.
MTC = Maximal tolerated concentration of BSO.
nd = not determined.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,177,263
Anderson, *Adv. Pharmacol.*, 38:65-78, 1997.
Anderson and Meister, *Proc. Natl. Acad. Sci. USA*, 80:707-711, 1983.
Burg et al., *Bioorg. Med. Chem.*, 10(1):195-205, 2002.
Campbell et al., *Anal. Biochem.*, 194:268-277, 1991.
Comess et al., *Biochemistry*, 31, 3975-3990, 1992.
Dikici et al., *Pediatr. Int.*, 43(6):577-580, 2001.
Eastman, In: *Cisplatin. Chemistry and Biochemistry of a Leading Anticancer Drug*, Lippert (ed.), Wiley-VCH, Zürich, Switzerland, 111-134, 1999.
Esmali et al., *Am. J. Ophthalmol.*, 132(6):945-947, 2001.
Garini et al., *Am. J. Kidney Dis.*, 38(6):E35, 2001.
Griffith, *J. Biol. Chem.*, 257:13704-13712, 1982.
Griffith and Meister, *J. Biol. Chem.*, 254:7558-7560, 1979.
Hatzakis et al., *J. Interferon. Cytokine Res.*, 21(10):861-869, 2001.
Jamieson and Lippard, *Chem. Rev.*, 99:2467-2498, 1999.
Johnson et al., *Prog. Clin. Biochem. Med.*, 10:1-24, 1989.
Kolokol'tsov et al., *Bull Exp. Biol. Med.*, 132(1):686-688, 2001.
Kunze, *Arch. Pharm.*, 329(11):503-509, 1996.
Lepre and Lippard, *Nucleic Acids Mol. Biol.*, 4:9-38, 1990.
Meister and Anderson, *Glutathione. Annl. Rev. Biochem.*, 52:711-760, 1983.
O'Dwyer et al., In: *Cisplatin. Chemistry and Biochemistry of a Leading Anticancer Drug*, Lippert (ed.), Wiley-VCH, Zürich, Switzerland, 31-72, 1999.
Reedijk, *Chem. Commun.*, 801-806, 1996.
Remington's Pharmaceutical Sciences, 15th ed., pages 624-652, Mack Publishing Company, Easton, Pa., 1980.
Remington's Pharmaceutical Sciences, 18th Ed. Mack Printing Company, pp. 1289-1329, 1990.
Richman and Meister, *J. Biol. Chem.*, 250:1422-1426, 1973.
Rosenberg, In: *Cisplatin. Chemistry and Biochemistry of a Leading Anticancer Drug*, Lippert (ed.), Wiley-VCH, Zürich, Switzerland, 3-30, 1999.
Tew, *Cancer Res.* 54(16):4313-4320, 1994.
Tew et al., *Adv. Drug Deliv. Rev.*, 26(2-3):91-104, 1997.
Zamble and Lippard, In: *Cisplatin. Chemistry and Biochemistry of a Leading Anticancer Drug*, Lippert (ed.), Wiley-VCH, Zürich, Switzerland, 73-110, 1999.

What is claimed is:

1. A composition comprising a compound represented by the structural formula or salts thereof, and a negative modulator of glutathione.

2. The composition of claim 1, wherein the negative modulator of glutathione is an inhibitor of glutathione synthesis.

3. The composition of claim 2, wherein the inhibitor of glutathione synthesis is an inhibitor of γ-glutamylcysteine synthetase.

4. The composition of claim 2, wherein the negative modulator of glutathione synthesis is L-buthionine-sulfoximine.

5. The composition of claim 1, wherein the negative modulator of glutathione is an inhibitor of glutathione transferase.

6. A composition comprising a compound represented by the structural formula or salts thereof, and a negative modulator of glutathione.

7. The composition of claim 6, wherein the negative modulator of glutathione is an inhibitor of glutathione synthesis.

8. The composition of claim 7, wherein the inhibitor of glutathione synthesis is an inhibitor of γ-glutamylcysteine synthetase.

9. The composition of claim 7, wherein the negative modulator of glutathione synthesis is L-buthionine-sulfoximine.

10. The composition of claim 6, wherein the negative modulator of glutathione is an inhibitor of glutathione transferase.

11. A composition comprising a compound represented by the structural formula or salts thereof, and a negative modulator of glutathione.

12. The composition of claim 11, wherein the negative modulator of glutathione is an inhibitor of glutathione synthesis.

13. The composition of claim 12, wherein the inhibitor of glutathione synthesis is an inhibitor of γ-glutamylcysteine synthetase.

14. The composition of claim 12, wherein the negative modulator of glutathione synthesis is L-buthionine-sulfoximine.

15. The composition of claim 11, wherein the negative modulator of glutathione is an inhibitor of glutathione transferase.

16. A composition comprising a compound represented by the structural formula or salts thereof, and a negative modulator of glutathione.

17. The composition of claim 16, wherein the negative modulator of glutathione is an inhibitor of glutathione synthesis.

18. The composition of claim 17, wherein the inhibitor of glutathione synthesis is an inhibitor of γ-glutamylcysteine synthetase.

19. The composition of claim 17, wherein the negative modulator of glutathione synthesis is L-buthionine-sulfoximine.

20. The composition of claim 16, wherein the negative modulator of glutathione is an inhibitor of glutathione transferase.

21. A pharmaceutical composition comprising (a) a platinum complex selected from the group consisting of ammine/cycloheptylamine-dichloro-platinum(II), ammine/piperidine-dichloro-platinum(II), ammine/hexamethyleneimine-dichloro-platinum(II), and ammine/hexamethyleneimine-tetrachloro-platinum(IV), and (b) a negative modulator of glutathione.

22. The pharmaceutical composition of claim 21, wherein the concentration of a selected platinum complex is in the approximate range of 0.1 mM to 20 mM.

23. The pharmaceutical composition of claim 21, wherein the concentration of a selected platinum complex is in the approximate range of 1 mM to 10 mM.

24. The pharmaceutical composition of claim 21, wherein the concentration of a selected platinum complex is in the approximate range of 1 mM to 5 mM.

25. The pharmaceutical composition of claim 21, wherein the negative modulator of glutathione is an inhibitor of glutathione synthesis.

26. The pharmaceutical composition of claim 25, wherein the inhibitor of glutathione synthesis is an inhibitor of γ-glutamylcysteine synthetase.

27. The pharmaceutical composition of claim 25, wherein the inhibitor of glutathione synthesis is L-buthionine-sulfoximine.

28. The pharmaceutical composition of claim 25, wherein the concentration of L-buthionine-sulfoximine is in the approximate range of 1 μM to 300 μM.

29. The pharmaceutical composition of claim 25, wherein the concentration of L-buthionine-sulfoximine is in the approximate range of 10 μM to 200 μM.

30. The pharmaceutical composition of claim 25, wherein the concentration of L-buthionine-sulfoximine is in the approximate range of 20 μM to 100 μM.

31. The pharmaceutical composition of claim 21, further defined as an intravenous pharmaceutical composition.

32. The pharmaceutical composition of claim 21, wherein the negative modulator of glutathione is an inhibitor of glutathione transferase.

33. A method of making ammine/cycloheptylamine-dichloro-platinum(II) comprising:
a) treating an aqueous 20 mmol solution of $K_2PtCl_4$ with 200 mmol KI with stirring for 10 minutes at room temperature; b) adding two equivalents of cycloheptylamine dropwise and stirring for 30 minutes forming a cis-$Pt^{II}$(c-$C_7H_{11}NH_2$)$_2I_2$ precipitate; c) filtering and washing the cis-$Pt^{II}$(c-$C_7H_{11}NH_2$)$_2I_2$ precipitate with water; d) recrystallizing the cis-$Pt^{II}$(c-$C_7H_{11}NH_2$)$_2I_2$ precipitate from a DMF/$H_2O$ mixture and washing with water, methanol, and ethyl ether; e) drying the cis-$Pt^{II}$(c-$C_7H_{11}NH_2$)$_2I_2$ precipitate in vacuo; f) suspending the dried cis-$Pt^{II}$(c-$C_7H_{11}NH_2$)$_2I_2$ precipitate in 50 mL of 60 to 70% $HClO_4$ and adding 150 mL of ethanol to the suspension with stirring at room temperature forming a brown [$Pt^{II}$(c-$C_7H_{11}NH_2$)$I_2$]$_2$ precipitate; g) filtering the brown [$Pt^{II}$(c-$C_7H_{11}NH_2$)$I_2$]$_2$ precipitate and washing the brown [$Pt^{II}$(c-$C_7H_{11}NH_2$)$I_2$]$_2$ precipitate with water; h) drying the washed brown [$Pt^{II}$(c-$C_7H_{11}NH_2$)$I_2$]$_2$ precipitate in vacuo; i) mixing 5 mmol of brown [$Pt^{II}$(c-$C_7H_{11}NH_2$)$I_2$]$_2$ precipitate with 5 mL of 1.5M $NH_4OH$ in 25 mL of water and stirring the mixture at room temperature overnight forming a yellow cis-$Pt^{II}(NH_3)(c-C_7H_{11}NH_2)I_2$ precipitate; j) filtering the yellow cis-$Pt^{II}(NH_3)(c-C_7H_{11}NH_2)I_2$ precipitate and washing with water; k) drying the washed yellow cis-$Pt^{II}(NH_3)(c-C_7H_{11}NH_2)I_2$ precipitate in vacuo 1) mixing 4 mmol of cis-$Pt^{II}(NH_3)(c-C_7H_{11}NH_2)I_2$ with 7.4 mmol of $AgNO_3$ in 200 mL of water and stirring overnight in the dark forming an AgI precipitate; m) removing AgI precipitate by filtration through celite forming a cis-$Pt^{II}(NH_3)(c-C_7H_{11}NH_2)NO_3$ filtrate; n) adding 10 mL of concentrated HCl the cis-$Pt^{II}(NH_3)(c-C_7H_{11}NH_2)NO_3$ filtrate and stirring the mixture for 3 h forming a yellow $Pt^{II}(NH_3)(C_7H_{11}N)Cl_2$ precipitate; o) evaporating the mixture to approximately 2 mL under reduced pressure and filtering yellow $Pt^{II}(NH_3)(C_7H_{11}N)Cl_2$ precipitate; p) washing the yellow $Pt^{II}(NH_3)(C_7H_{11}N)Cl_2$ precipitate with water and acetone, and drying the washed yellow $Pt^{II}(NH_3)(C_7H_{11}N)Cl_2$ precipitate in vacuo.

34. A method of making ammine/hexamethyleneimine-tetrachloro-platinum(IV) comprising:

a) adding 10 milliliters of $H_2O_2$ to a suspension of 2.61 mmol $Pt^{II}(NH_3)(C_6H_{13}N)Cl_2$ in 200 mL of water, stirring for 15 hours, filtering the solution, concentrating to a minimum volume b) precipitating with acetone forming a yellow ($Pt^{IV}(NH_3)(C_6H_{13}N)$trans-$(OH)_2Cl_2$) product; c) drying the yellow ($Pt^{IV}(NH_3)(C_6H_{13}N)$trans-$(OH)_2Cl_2$) in vacuo.

d) dissolving the yellow 1.64 mmol of $Pt^{IV}(NH_3)(C_6H_{13}N)$trans-$(OH)_2Cl_2$ (0.650 g; 1.64 mmol) in 100 mL of water; e) adding 20 mL of concentrated HCl and stirring for 24 hours at room temperature forming a clear yellow solution; f) filtering the clear yellow solution, concentrating the clear yellow solution to a minimum volume to form a yellow crystalline $Pt^{IV}(NH_3)(C_6H_{13}N)Cl_4$; and g) filtering, washing the yellow crystalline $Pt^{IV}(NH_3)(C_6H_{13}N)Cl_4$ with water, and drying under a vacuum.

\* \* \* \* \*

UNITED STATES PATENT AND TRADEMARK OFFICE
CERTIFICATE OF CORRECTION

PATENT NO.       : 7,271,161 B2
APPLICATION NO.  : 10/655657
DATED            : September 18, 2007
INVENTOR(S)      : Zahid H. Siddik et al.

It is certified that error appears in the above-identified patent and that said Letters Patent is hereby corrected as shown below:

In claim 33, column 24, line 56, delete "$Pt_{II}$" and insert --$Pt^{II}$-- therefor.

In claim 33, column 24, line 64, delete "$Pt_{II}$" and insert --$Pt^{II}$-- therefor.

In claim 33, column 25, line 6, delete "$Pt_{II}$" and insert --$Pt^{II}$-- therefor.

In claim 33, column 25, line 11, delete "$Pt_{II}$" and insert --$Pt^{II}$-- therefor.

In claim 33, column 25, line 18, delete "$Pt_{II}$" and insert --$Pt^{II}$-- therefor.

In claim 34, column 26, line 10, delete "$Pt_{IV}$" and insert --$Pt^{IV}$-- therefor.

In claim 34, column 26, line 18, delete "$Pt_{IV}$" and insert --$Pt^{IV}$-- therefor.

Signed and Sealed this

Eleventh Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,271,161 B2
APPLICATION NO. : 10/655657
DATED : September 18, 2007
INVENTOR(S) : Zahid H. Siddik et al.

It is certified that error appears in the above-identified patent and that said Letters Patent is hereby corrected as shown below:

In column 1, lines 10-12, delete
"The government may own rights in the present invention pursuant to grant number RO1CA50380 from the National Cancer Institute." and insert
--This invention was made with government support under CA050380 awarded by The National Institutes of Health. The government has certain rights in the invention.--
therefor.

Signed and Sealed this

Twenty-first Day of April, 2009

JOHN DOLL
*Acting Director of the United States Patent and Trademark Office*